United States Patent [19]

Yamada et al.

[11] Patent Number: 5,585,460
[45] Date of Patent: Dec. 17, 1996

[54] BIODEGRADABLE HIGH-MOLECULAR POLYMERS, PRODUCTION AND USE THEREOF

[75] Inventors: Minoru Yamada, Kawanishi; Toshiro Heya, Takarazuka; Yasuaki Ogawa, Otokuni-gun, all of Japan

[73] Assignee: Takeda Chemical Industries, Ltd., Osaka, Japan

[21] Appl. No.: 270,791

[22] Filed: Jul. 5, 1994

Related U.S. Application Data

[63] Continuation of Ser. No. 684,270, Apr. 12, 1991, abandoned.

[30] Foreign Application Priority Data

Apr. 13, 1990 [JP] Japan ................................. 2-098510

[51] Int. Cl.⁶ ........................................................ C08G 63/08
[52] U.S. Cl. ................................................ 528/491; 528/499
[58] Field of Search ............................... 528/361, 354, 528/480, 491, 499, 502 R

[56] References Cited

U.S. PATENT DOCUMENTS

| 4,389,330 | 1/1983 | Tice et al. ................................. 424/33 |
| 4,728,721 | 3/1988 | Yamamoto et al. ..................... 528/499 |
| 4,810,775 | 3/1989 | Bendix et al. .......................... 528/499 |
| 4,853,224 | 8/1989 | Wong ...................................... 424/427 |
| 5,041,529 | 8/1991 | Shinoda et al. ........................ 528/354 |
| 5,182,258 | 1/1993 | Chiou ......................................... 514/3 |

FOREIGN PATENT DOCUMENTS

| 0026599 | 4/1981 | European Pat. Off. . |
| 0145240 | 6/1985 | European Pat. Off. . |
| 0190833 | 8/1986 | European Pat. Off. . |
| 0202065 | 11/1986 | European Pat. Off. . |
| 0283925 | 9/1988 | European Pat. Off. . |
| 2491351 | 4/1982 | France . |

*Primary Examiner*—Jeffrey Mullis
*Attorney, Agent, or Firm*—Foley & Lardner

[57] ABSTRACT

The invention provides a method of purifying biodegradable aliphatic polyesters which comprises dissolving, in a readily water-soluble organic solvent, a biodegradable aliphatic polyester which contains low-molecular substances and adding water to the resulting solution to thereby remove said low-molecular substances, biodegradable aliphatic polyesters obtained by said method and containing low-molecular substances with a molecular weight of 1,000 or less in an amount of not higher than 3%, and drug-containing compositions which comprise any of said biodegradable polyesters.

4 Claims, No Drawings

BIODEGRADABLE HIGH-MOLECULAR POLYMERS, PRODUCTION AND USE THEREOF

This application is a continuation of United States application Ser. No. 07/684,270 filed Apr. 12, 1991, now abandoned.

FIELD OF THE INVENTION

This invention relates to biodegradable (degradable in vivo as much as in vitro) high-molecular polyesters useful as bases for pharmaceutical preparations, to a method of producing the same and to a use of the same.

BACKGROUND OF THE INVENTION

Biodegradable high-molecular polymers can be used, for example, as bases for such pharmaceutical preparations as microcapsules. U.S. Pat. No. 4,683,288, for instance, describes that polycondensation of lactic acid and/or glycolic acid in the presence or absence of a catalyst gives polymers or copolymers of these as biodegradable high-molecular polymers.

U.S. Pat. No. 4,767,628 discloses a method of producing sustained release microcapsules in which such biodegradable high-molecular polymers are used. Furthermore, U.S. Pat. No. 4,728,721 describes that the initial release of a drug from microcapsules can be decreased by removing readily water-soluble low-molecular compounds from biodegradable high-molecular polymer solutions by washing with water.

Sustained-release preparations produced by dispersing a drug in a biodegradable high-molecular polymer should desirably be capable of releasing the drug at a voluntarily controlled rate. Generally, the drug release period of a sustained-release preparation is adjusted by the molecular weight of the biodegradable high-molecular polymer, which serves as the base for said preparation. In most cases, however, the initial drug release is too great although said release may vary depending on the kind and amount of the polymer.

The removal of readily water-soluble low-molecular compounds by the above-mentioned method of U.S. Pat. No. 4,728,721 indeed results in an improved initial release. The extent of improvement, however, is such that it is impossible to suppress only the initial release and thereby increase the rate of release in later stages although it is possible to maintain the rate of drug release at a nearly constant level throughout the whole release period.

As a result of intensive investigations made in an attempt to solve the above problems, it was found that a relatively low-molecular fraction of the biodegradable high-molecular polymer is deeply involved in the initial release.

Thus, it was found that the high-molecular polymer produced by the polymerization reaction (cf. U.S. Pat. Nos. 4,683,288 and 4,728,721) contains a large amount of oligomers with a molecular weight of 1,000 or less as well as the starting monomer or monomers. It was revealed that such a relatively low-molecular fraction causes an excess initial release from preparations in which said high-molecular polymer is used as the wall substance.

Ordinary purification methods such as washing with water cannot eliminate the relatively low-molecular fraction (oligomers) mentioned above from the high-molecular polymer. As a result of intensive investigations, the present inventors found a method which enables the removal of said fraction and have now completed the present invention.

SUMMARY OF THE INVENTION

The invention provides a method of purifying biodegradable aliphatic polyesters which comprises dissolving, in a readily water-soluble organic solvent, a biodegradable aliphatic polyester which contains low-molecular substances and adding water to the resulting solution to precipitate high-molecular substances and to thereby remove said low-molecular substances, biodegradable aliphatic polyesters obtained by said method and containing low-molecular substances with a molecular weight of 1,000 or less in an amount of not higher than 3%, and drug-containing compositions which comprise any of said biodegradable polyesters.

DETAILED DESCRIPTION OF THE PREFERRED EMBODIMENT

The term "molecular weight" as used herein means the molecular weight on the polystyrene basis as determined by gel permeation chromatograhy (GPC) using polystyrene species as standard substances.

The biodegradable aliphatic polyester to which the method of the invention is to be applied should preferably have good biocompatibility and includes, among others, polycondensation polyesters, such as polyglycolic acid, polylactic acid, polyhydroxybutyric acid, polyhydroxypivalic acid and polymalic acid, and ring-opening polymerization polyesters, such as polyglycolide, polylactide, poly-$\beta$-propiolactone, poly-$\delta$-butyrolactone and poly-$\epsilon$-caprolactone. In particular, the method can be advantageously applied to the purification of polycondensation polyesters derived from hydroxy-aliphatic carboxylic acids.

Said polyesters are not limited to the homopolymers given above as examples but of course include copolymers composed of two or more constituents. The manner of copolymerization may be random, block or graft.

Among these high-molecular polymers (polyesters), those that undergo relatively rapid degradation in vivo are preferred.

As preferred examples of the biodegradable aliphatic polyester of this invention, there may be mentioned polylactic acid and lactic acid-glycolic acid copolymers, and polyhydroxybutylic acid and hydroxybutyric acid-glycolic acid copolymers. The lactic acid-glycolic acid copolymers may have a composition such that lactic acid accounts for 100-50 mole percent with the balance being glycolic acid. The hydroxybutyric acid-glycolic acid copolymers may have a composition such that hydroxybutyric acid accounts for 100-25 mole percent with the balance being glycolic acid.

Furthermore, preferred among such lactic acid-glycolic acid copolymers and hydroxybutyric acid-glycolic acid copolymers are those showing a molecular weight peak (in GPC) within the range of 3,000–50,000, more preferably 5,000–30,000.

The readily water-soluble organic solvent to be used in the practice of the invention is, for example, acetone, tetrahydrofuran, dioxane, dimethylformamide, or dimethyl sulfoxide. The use of acetone is particularly advantageous.

In the practice of the invention, the quantity of water relative to the quantity of the biodegradable high-molecular polymer solution is not critical. If the quantity of water is excess, however, the removal of low-molecular polymers may become insufficient. If, conversely, said quantity is too small, the recovery of the biodegradable high-molecular polymer may become decreased. Generally, 50–150 parts (by volume) of water is used per 100 parts of the readily water-soluble organic solvent. Upon gradual addition of water to the biodegradable high-molecular polymer solution with stirring by an appropriate means, the desired biodegradable high-molecular polymer precipitates out or separates out. The resulting precipitate or oil layer is recovered by an appropriate method, washed with water to a sufficient extent and then dried.

In cases where one dissolution-precipitation step is insufficient for the removal of low-molecular polymers, the dissolution-precipitation step should be repeated a plurality of times.

The biodegradable high-molecular polymer obtained by the method of this invention can be used, for example, as the base (the wall substance) for microcapsules. Thus, for instance, sustained release microcapsules containing a water-soluble drug can be produced by preparing a water-in-oil (W/O) type emulsion using, as the inner aqueous phase, an aqueous solution of a water-soluble polypeptide, such as luteinizing hormone releasing hormone, its analog (cf. U.S. Pat. Nos. 3,853,837, 4,008,209, 3,972,859, 4,234,571 and 4,652,441), thyrotropin releasing hormone, its salts, and derivatives thereof (cf. U.S. Pat. Nos. 3,957,247, 4,100,152 and 4,100,274), with addition, if necessary or where appropriate, of a drug-retaining or drug-holding substance, such as gelatin, albumin, pectin or agar, to said inner aqueous phase, and, as the oil phase, a solution containing the biodegradable high-molecular polymer obtained in accordance with the invention and dispersing said emulsion in an aqueous phase to give a W/O type emulsion, followed by drying in water.

The microcapsules produced by the method according to the invention can be administered as they are to living organisms as implants. They can also be administered in various dosage forms or can be used as raw materials in the manufacture of such dosage forms.

The dosage forms mentioned above include injections, oral preparations, nasal preparations, and rectal, urethral and vaginal suppositories, among others.

In making up the microcapsules according to the invention into injections, for instance, the microcapsules according to the invention are made up into a practically usable sustained release injection in the form of an aqueous suspension together with a dispersing agent (e.g. Tween 80, HCO-60, carboxymethyl-cellulose, sodium alginate), a preservative (e.g. methylparaben, propylparaben), an isotonizing agent (e.g. sodium chloride, mannitol, sorbitol, glucose), and so on or in the form of an oleaginous suspension together with a vegetable oil such as sesame oil or corn oil.

Furthermore, more stable, injectable, sustained release preparations containing the above-mentioned microcapsules for use in the suspension form, other than the above-mentioned formulations, are obtained by the steps of adding one or more excipients (e.g. mannitol, sorbitol, lactose, glucose), redispersing, and solidifying by freeze drying or spray drying, with distilled water for injection or an appropriate dispersion medium being attached.

The dose of such sustained release preparations provided by the present invention may vary depending on the kind and content of the active ingredient peptide, the dosage form, the duration of drug release, the target animal [e.g. warm-blooded mammal (e.g. mouse, rat, horse, cattle, human)] and the purpose of administration but should at least correspond to the effective dose of said active ingredient. Thus, for example, the single dose for a mammal such as mentioned above can suitably be selected preferably within the range of about 0.1 mg to 100 mg per kilogram of body weight, more preferably within the range of about 0.2 mg to 50 mg per kilogram of body weight, in terms of the microcapsule weight. The volume of the suspension in administering the above-mentioned injections can suitably be selected within the range of about 0.1 to 5 ml, preferably about 0.2 to 3.0 ml.

In addition to microcapsules, sustained release preparations in spherical, cylindrical, needle-shaped or some other form can also be produced by melting a composition comprising the biodegradable high-molecular polymer according to the invention and a drug dispersed therein by an appropriate method and molding the melt.

OPERATION AND EXAMPLES

The following comparative examples and working examples are further illustrative of the present invention.

Comparative Example 1

A 1,000-ml four-necked flask equipped with a nitrogen inlet tube and a condenser was charged with 375.3 g of 90% lactic acid and 95.1 g of glycolic acid. The charge was heated in a nitrogen atmosphere under reduced pressure from 90° C. and 400 mmHg to 150° C. and 30 mmHg over 5 hours for removing the distillate water. Further heating under reduced pressure at 5–7 mmHg and 150°–175° C. for 24 hours followed by cooling gave an amber-colored lactic acid-glycolic acid copolymer.

The copolymer thus obtained was dissolved in 1,000 ml of dichloromethane and the solution was poured into warm water (60° C.) with stirring. The resulting dough-like high-molecular polymer that had separated out was collected and dried in vacuo at 30° C.

The thus-obtained lactic acid-glycolic acid copolymer, when analyzed by GPC, showed a molecular weight peak at 10,000 and a low-molecular polymer (molecular weight 1,000 or less) content of 6.8%.

Comparative Example 2

TRH (thyrotropin releasing hormone; 350 mg) was dissolved in 0.625 ml of distilled water and the solution was added to a solution of 5 g of the lactic acid-glycolic acid copolymer (PLGA) obtained in Comparative Example 1 in 6.25 ml of dichloromethane. The mixture was homogenized in a small-sized homogenizer for 60 seconds to give a W/O type emulsion. This emulsion was cooled to 18° C. and then poured into 1,250 ml of a 0.25% aqueous solution of polyvinyl alcohol (PVA) adjusted in advance to 18° C., and the mixture was homogenized using a turbine-type homo-mixer to give a W/O/W type emulsion. The dichloromethane was evaporated by stirring the W/O/W type emulsion at room temperature for solidification of the inner W/O type emulsion. The resulting microcapsules were collected by centrifugation, dispersed again in distilled water and further centrifuged for washing away the free drug portion etc.

Freeze drying of the microcapsules obtained gave a powder. The microcapsules obtained were tested for drug trapping percentage and for in vitro dissolution into a phosphate buffer having a pH of 7.0 at 37° C. The results are shown in Table 1.

Comparative Example 3

A 1,000-ml four-necked flask equipped with a nitrogen inlet tube and a condenser was charged with 375.3 g of 90% lactic acid and 95.1 g of glycolic acid and the charge was heated in a nitrogen atmosphere under reduced pressure from 90° C. and 400 mmHg to 150° C. and 30 mmHg over 5 hours for removing the distillate water. Further heating under reduced pressure at 5–7 mmHg and 150°–175° C. for 36 hours and the subsequent cooling gave an amber-colored lactic acid-glycolic acid copolymer.

The copolymer thus obtained was dissolved in 1,000 ml of dichloromethane and the solution was poured into warm water (60° C.) with stirring, whereupon a dough-like high-molecular polymer separated out. This polymer was collected and dried in vacuo at 30° C.

The thus-obtained lactic acid-glycolic acid copolymer, when analyzed by GPC, showed a molecular weight peak at 13,000 and a low-molecular polymer (molecular weight 1,000 or less) content of 5.5%.

Comparative Example 4

A LHRH analog (luteinizing hormone releasing hormone, leuprolide acetate; 450 mg) and 40 mg of gelatin were dissolved in 0.8 ml of distilled water and the solution was added to a solution of 3.5 g of the lactic acid-glycolic acid copolymer obtained in Comparative Example 3 in 5 ml of dichloromethane. The mixture was homogenized in a small-sized homogenizer for 60 seconds to give a W/O type emulsion. This emulsion was cooled to 18° C. and then poured into 200 ml of a 0.5% aqueous solution of polyvinyl alcohol (PVA) adjusted in advance to 18° C., and the mixture was homogenized in a turbine-type homogenizer to give a W/O/W type emulsion. This W/O/W type emulsion was stirred at room temperature for evaporating the dichloromethane and solidifying the inner W/O type emulsion. The resulting solid was collected using a centrifuge. This was again dispersed in distilled water for washing away the drug portion remaining in free form, among others, and then recovered by centrifugation.

Freeze-drying of the microcapsules collected gave a powder. The microcapsules obtained were tested for drug trapping percentage and for in vitro dissolution into a phosphate buffer having a pH of 7.0 at 37° C. The results are shown in Table 2.

Example 1

Twenty grams (20 g) of the lactic acid-glycolic acid copolymer obtained in Comparative Example 1 was dissolved in 100 ml of acetone. Distilled water (60 ml) was added dropwise to the solution with stirring. The oil layer that separated out was collected and washed with two 500-ml portions of distilled water, whereupon the oil layer turned into a dough-like matter. This was dried in vacuo at 30° C. The yield was 17.4 g.

The thus-obtained lactic acid-glycolic acid copolymer, when analyzed by GPC, showed a peak molecular weight value of 10,000 and a low-molecular polymer (molecular weight 1,000 or less) fraction content of 2.0%.

Example 2

Microcapsules were prepared in the same manner as in Comparative Example 2 using the lactic acid-glycolic acid copolymer obtained in Example 1. The microcapsules obtained were tested for drug trapping percentage and for in vitro dissolution into a phosphate buffer having a pH of 7.0 at 37° C. The results are shown in Table 1.

TABLE 1

|  | Trapping percentage (%)[a] | Release percentage (%)[b] | | |
|---|---|---|---|---|
|  |  | 1 day | 1 week | 2 weeks |
| Comparative Example 2 | 93.0 | 8.8 | 47.8 | 95.2 |
| Example 2 | 93.6 | 5.7 | 27.8 | 77.6 |

[a] Amount of TRH actually taken up relative to the charged amount of TRH.
[b] pH 7.0, 1/30M phosphate buffer, 37° C.

Example 3

Twenty grams (20 g) of the lactic acid-glycolic acid copolymer obtained in Comparative Example 3 was dissolved in 100 ml of acetone. Distilled water (60 ml) was added dropwise to the solution with stirring. The oil layer that separated out was collected and washed with two 500-ml portions of distilled water, whereupon the oil layer turned into a dough-like matter. This was dried in vacuo at 30° C. The yield was 17.4 g.

The lactic acid-glycolic acid copolymer thus obtained, when analyzed by GPC, showed a peak molecular weight value of 13,000 and a low-molecular polymer (molecular weight 1,000 or less) fraction content of 2.2%.

Example 4

Microcapsules were prepared in the same manner as in Comparative Example 4 using the lactic acid-glycolic acid copolymer obtained in Example 3. The microcapsules obtained were tested for drug trapping percentage and for in vitro dissolution into a phosphate buffer having a pH of 7.0 at 37° C. The results are shown in Table 2.

TABLE 2

|  | Trapping percentage (%)[a] | Release percentage (%)[b] | | | | |
|---|---|---|---|---|---|---|
|  |  | 1 day | 1 week | 2 weeks | 3 weeks | 4 weeks |
| Comparative Example 4 | 95.0 | 10.4 | 30.7 | 41.3 | 59.5 | 65.2 |
| Example 4 | 97.2 | 4.8 | 9.7 | 24.5 | 41.2 | 55.7 |

[a] Amount of the LHRH analog actually taken up relative to the charged amount.
[b] pH 7.0, 1/30M phosphate buffer, 37° C.

Comparative Example 5

A 1,000 ml four-necked flask fitted with a nitrogen gas inlet tube and condenser was charged with 190.2 g of glycolic acid and 260.2 g of D,L-2-hydroxybutyric acid and the charge was heated under a nitrogen blanket at a reduced pressure of 400 mmHg and 90° C. to 30 mmHg and 150° C. over a period of 5 hours, with the distillate water being removed. Then, the vacuum heating was continued at 5–7 mmHg and 150°–185° C. for 72 hours, followed by cooling to give a glycolic acid-2-hydroxybutyric acid copolymer as an amber-colored substance.

This polymer was dissolved in 1,000 ml of dichloromethane and poured in warm water at 60° C. with stirring. The dough-like polymer that had separated out was collected and dried in vacuo at 30° C.

The glycolic acid-2-hydroxybutyric acid copolymer having the copolymer ratio of 50/50 thus obtained had a peak molecular weight value of 12,000 as determined by GPC and contained 5.2% of low molecular polymers having molecular weights not exceeding 1,000.

Comparative Example 6

In 0.3 ml of distilled water was dissolved 350 mg of TRH (thyrotropin-releasing hormone) and this solution was added to a solution prepared by dissolving 4.65 g of the glycolic acid-2-hydroxybutyric acid copolymer (the copolymer ratio, 50/50) obtained in Comparative Example 5 in 5 ml of dichloromethane. The mixture was homogenized in a compact homogenizer for 60 seconds to give a W/O emulsion. This emulsion was cooled to 18° C. and poured in 1,000 ml of a 0.1% aqueous solution of polyvinyl alcohol (PVA) preadjusted to 18° C. The mixture was homogenized in a turbine homo-mixer to give a W/O/W emulsion. This W/O/W emulsion was stirred at room temperature to evaporate the dichloromethane and solidify the internal W/O emulsion, which was then collected using a centrifuge. This emulsion was redispersed in distilled water and centrifuged to wash the free drug etc.

The microcapsules thus collected were lyophilized to give a powder. The drug trapping rate of the resulting microcapsules and the result of an in vitro dissolution test performed in phosphate buffer, pH 7.0, at 37° C. are set forth in Table 3.

Example 5

In 100 ml of acetone was dissolved 20 g of the glycolic acid-2-hydroxybutyric acid copolymer (the copolymer ratio, 50/50) obtained in Comparative Example 5. While this solution was stirred, 80 ml of distilled water was added dropwise. The resulting oil layer was collected and washed with 500 ml of distilled water twice, whereby the oil layer became dough-like. This was dried in vacuo at 30° C. The yield was 18.1 g.

This glycolic acid-2-hydroxybutyric acid copolymer having the copolymer ratio of 50/50, had a peak molecular weight value of 13,000 as determined by GPC and contained 2.5% of low molecular polymers having molecular weights not exceeding 1,000.

Example 6

Using the glycolic acid-2-hydroxybutyric acid copolymer (the copolymer ratio, 50/50) obtained in Example 5, microcapsules were prepared in the same manner as in Comparative Example 6. The drug trapping rate of the microcapsules and the result of an in vitro dissolution test performed in phosphate buffer, pH 7.0, at 37° C. are set forth in Table 3.

TABLE 3

| | Trapping rate (%)[a] | Rate of release (%)[b] | | | |
|---|---|---|---|---|---|
| | | one day | one week | two weeks | three weeks |
| Comparative Example 6 | 85.6 | 17.3 | 50.1 | 89.7 | 99.8 |
| Example 6 | 95.6 | 9.0 | 40.5 | 85.1 | 99.9 |

[a]The amount of TRH actually incorporated relative to the feed.
[b]1/30M phosphate buffer, pH 7.0, 37° C.

Comparative Example 7

A 1,000 ml four-necked flask fitted with a nitrogen gas inlet tube and condenser was charged with 450 g of D,L-lactic acid and the charge was heated under a nitrogen blanket at 90° C., 400 mmHg to 150° C., 30 mmHg over a period of 5 hours, with the distillate water being removed. The vacuum heating was further continued at 5–7 mmHg and 150°–180° C. for 23 hours, followed by cooling to give polylactic acid as a pale yellow product.

In 1,000 ml of dichloromethane was dissolved the above polylactic acid and the solution was stirred into warm water at 60° C. The resulting dough-like high polymer was collected and dried in vacuo at 30° C.

This polylactic acid had a peak molecular weight value of 8,000 as determined by GPC and contained 5.8% of low molecular polymers having molecular weights not exceeding 1,000.

Comparative Example 8

In 0.4 ml of distilled water was dissolved 400 mg of a LHRH analog (luteinizing hormone-releasing hormone, leuprolide acetate) and this solution was added to a solution prepared by dissolving 4.0 g of the polylactic acid obtained in Comparative Example 7 in 5 ml of dichloromethane. The mixture was homogenized in a compact homogenizer for 60 seconds to give a W/O emulsion. This emulsion was cooled to 18° C. and poured in 1,000 ml of a 0.1% aqueous solution of polyvinyl alcohol (PVA) preadjusted to 18° C. and the mixture was homogenized with a turbine homo-mixer to give a W/O/W emulsion. This W/O/W emulsion was then stirred at room temperature to evaporate the dichloromethane and solidify the internal W/O emulsion, which was then collected by centrifugation. This solid emulsion was redispersed in distilled water and further centrifuged to wash out the free drug etc.

The microcapsules thus collected were lyophilized to give a powder. The drug trapping rate of the microcapsules and the result of an in vitro dissolution test performed in phosphate buffer, pH 7.0, at 37° C. are set forth in Table 4.

Example 7

In 100 ml of acetone was dissolved 20 g of the polylactic acid obtained in Comparative Example 7. While this solution was stirred, 80 ml of distilled water was added dropwise. The resulting oil layer was collected and washed with 500 ml of distilled water twice, whereby the oil layer became paste-like. This product was dried in vacuo at 30° C. The yield was 18.5 g.

The polylactic acid had a peak molecular weight value of 8,000 as determined by GPC and contained 2.3% of low molecular polymers having molecular weights not exceeding 1,000.

Example 8

Using the polylactic acid obtained in Example 7, microcapsules were prepared in the same manner as in Comparative Example 8. The drug trapping rate of the microcapsules and the result of an in vitro dissolution test performed in phosphate buffer, pH 7.0, at 37° C. are set forth in Table 4.

TABLE 4

| | Trapping rate (%)[a] | Rate of release (%)[b] | | | |
|---|---|---|---|---|---|
| | | one day | one week | two weeks | three weeks |
| Comparative Example 8 | 92.5 | 22.4 | 36.8 | 44.1 | 56.8 |
| Example 8 | 98.6 | 8.4 | 18.2 | 28.5 | 48.2 |

[a] The amount of the LHRH analog actually incorporated relative to the feed.
[b] 1/30M phosphate buffer, pH 7.0, 37° C.

What is claimed is:

1. A method of purifying a biodegradable aliphatic polyester produced without using a catalyst and separated out and collected after polymerization reaction, comprising about 50 to 100 mole percent of lactic acid and about 50 to 0 mole percent of glycolic acid, having a weight average molecular weight of about 3,000 to 50,000 as determined by gel permeation chromatography with a polystyrene standard and containing oligomers having a molecular weight up to 1,000 as determined by gel permeation chromatography with a polystyrene standard, said method comprising:

(a) dissolving, in 100 parts by volume of a water-soluble organic solvent, a crude biodegradable aliphatic polyester which contains said oligomers to produce a solution, (b) gradually adding 50 to 150 parts by volume of water to the solution with stirring, (c) recovering a resulting precipitate or oil layer, and (d) washing the recovered precipitate or oil layer with water to obtain a purified biodegradable aliphatic polyester containing equal to or less than 3% by weight of oligomers.

2. The method according to claim 1, wherein both lactic acid and glycolic acid are present in the biodegradable aliphatic polyester.

3. The method according to claim 1, wherein the water-soluble organic solvent is a member selected from the group consisting of acetone, tetrahydrofuran, dioxane, dimethylformamide and dimethylsulfoxide.

4. The method according to claim 3, wherein the readily water-soluble organic solvent is acetone.

* * * * *